United States Patent [19]

Gordon et al.

[11] 4,332,369

[45] Jun. 1, 1982

[54] ADJUSTABLE IN-LINE INTRAVENOUS VALVE WITH LOCKING MECHANISM

[75] Inventors: Marvin Gordon, East Windsor; Joseph Lichtenstein, Colonia, both of N.J.

[73] Assignee: Whitman Medical Corporation, Clark, N.J.

[21] Appl. No.: 168,722

[22] Filed: Jul. 14, 1980

[51] Int. Cl.$^3$ .............................................. F16K 35/02
[52] U.S. Cl. .................................. 251/114; 251/205; 251/267; 251/297; 74/530; 74/527; 74/25; 128/214 C; 128/274
[58] Field of Search ........................ 128/214 C, 274; 251/114, 115, 95, 98, 205, 208, 209, 297, 267, 268, 86, 319, 248, 250.5, 326; 137/383, 385; 74/25, 527, 530

[56] References Cited

U.S. PATENT DOCUMENTS

| | | | |
|---|---|---|---|
| 745,152 | 11/1903 | Chesbro | 251/115 |
| 797,922 | 8/1905 | Sherman | 251/297 |
| 1,379,904 | 5/1921 | Derby | 251/115 |
| 2,198,639 | 4/1940 | Stines | 251/114 |
| 2,199,158 | 4/1940 | Hein et al. | 251/250.5 |
| 2,784,934 | 3/1957 | Paulius, Jr. et al. | 251/297 |
| 3,289,999 | 12/1966 | Konzak | 251/297 |
| 3,326,513 | 6/1967 | Hall | 251/86 |
| 3,332,439 | 7/1967 | Burke | 251/297 |
| 3,877,428 | 4/1975 | Seagle et al. | 251/208 |
| 4,140,297 | 2/1979 | Bussell | 251/208 |
| 4,230,300 | 10/1980 | Wiltse | 251/205 |

FOREIGN PATENT DOCUMENTS

427900 12/1947 Italy ................................. 251/114

Primary Examiner—George L. Walton
Attorney, Agent, or Firm—Holman & Stern

[57] ABSTRACT

An intravenous flow control valve includes an in-line valving mechanism as opposed to a tube clamp. The mechanism includes an adjustment member and a locking mechanism for selectively locking the adjustment member in place and thereby assure accurate flow rate settings.

8 Claims, 5 Drawing Figures

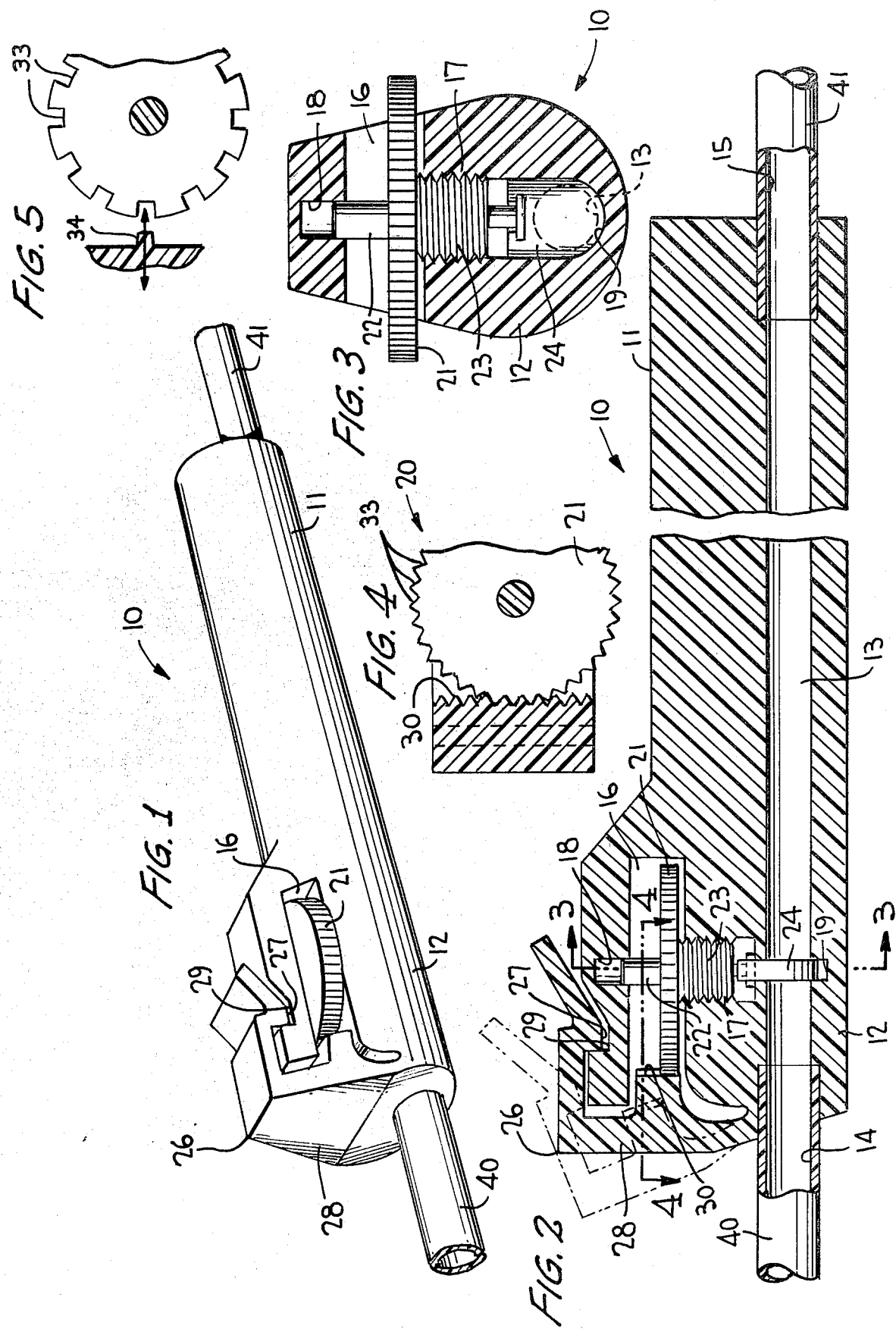

ADJUSTABLE IN-LINE INTRAVENOUS VALVE WITH LOCKING MECHANISM

TECHNICAL FIELD

The present invention relates to control valves in system for parenteral fluid infusion. More specifically, the present invention relates to a valve which, although simple and inexpensive to manufacture, permits accurate and reliable adjustable settings of intravenous liquid flow rate.

BACKGROUND OF THE INVENTION

In administering intravenous fluids to a patient, control of flow rate is critical. If the amount of administered fluid delivered in a given period of time varies considerably from the prescribed dosage rate, the results can be of serious consequence and are often fatal. The most common types of adjustable flow control used today is a clamp device which pinches the IV (intravenous) tubing by an adjustable amount. It has been well documented in the medical literature (see "Flow Rate Maintenance and Output Intravenous Fluid Test Sets", Demorouelle et al, American Journal of Hospital Pharmacy, Vol. 32, pages 177–185, February 1975; and "Regulatory Intravenous Fluid Flow: Controller versus Clamps", Ziser et al, American Journal of Hospital Pharmacy, Vol. 36, pages 1090–1094, August 1979) that such clamps are unable to maintain constant flow rates for any reasonable period of time. The main cause of the problem in this regard is "creep", a phenomenon wherein the plastic tubing diameter, when under stress, continues to change. In addition, the settings of these prior art IV clamps are accessible to curious patients and susceptible to variation upon movement by the patient. Thus, while adjustable IV clamps are very inexpensive, they represent a considerable sacrifice when it comes to maintaining accurate dosage rates.

On the other end of the cost spectrum, the prior art contains automatic systems for precisely maintaining selectable IV flow rates. These systems are generally made up of electrical pumps, sensors and controllers and, for most applications, are prohibitively expensive. As a consequence, it is estimated that sales of such systems comprise less than ten percent of the available market, whereas the much less accurate but inexpensive adjustable clamps account for substantially all other sales.

Still another approach to adjustable IV flow control is in the in-line valve characterized by a valving mechanism which is adjustably inserted directly into the flow path of the IV fluid. Examples of in-line IV valves may be found in U.S. Pat. Nos. 3,880,401 (Waltse); 4,079,737 (Miller); 3,877,428 (Seagle et al); and 3,868,973 (Bierman et al). Such in-line valves tend to be more accurate than the adjustable clamp and far less expensive than the automatic control system. However, such in-line valves have not obtained a meaningful share of the relevant market for two primary reasons. First, the in-line valves are sufficiently more complex and expensive to manufacture than the clamp valves as to make comparative cost an important factor to the user. Second, although not subject to the "creep" phenomenon, the in-line valve is still subject to twiddling by a curious patient and to inadvertent setting variation during patient movement or inadvertent manipulation by health care personnel.

SUMMARY OF THE INVENTION

It is therefore an object of the present invention to provide an inexpensive device of controlling IV flow rate which provides an accurate and maintainable setting and which is not subject to inadvertent setting variation. It is a further object of the present invention to provide a device of the type described wherein setting changes by curious patients are considerably minimized.

In accordance with the present invention, an inexpensively fabricated IV control valve includes an elongated body member having a longitudinal bore passage defined therethrough and adapted for connection in an IV line. A sluice gate type of valve is adjustably positioned in the bore passage by means of a bolt which threadably engages a bore in the handle and is controlled by an adjustment knob. The adjustment knob is positioned to be easily turned between the user's thumb and forefinger when the member is grasped in the user's palm. A brake lock, preferably formed as an integral part of the handle member, is arranged to snap into a locking position wherein a brake surface is urged against the adjustment knob to prevent movement of the knob and maintain a constant valve setting. Other forms of valve locking may be used.

BRIEF DESCRIPTION OF THE DRAWINGS

The embodiments of the present invention will become more clear when taken in conjuction with the drawings, wherein:

FIG. 1 is a view in perspective of the valve and locking mechanism of the present invention;

FIG. 2 is a plan view in section of the valve and locking mechanism of FIG. 1;

FIG. 3 is a view in section taken along lines 3—3 of FIG. 2;

FIG. 4 is a view in section taken along lines 4—4 of FIG. 2; and

FIG. 5 is a view similar to FIG. 4 of a different locking mechanism suitable for use in the present invention.

DESCRIPTION OF THE PREFERRED EMBODIMENTS

Referring more specifically to the drawings, the valve of the present invention includes an elongated body member generally designated by the reference numeral 10. Body member 10 and other valve parts described below can be made from plastic polymers, nylon, teflon, stainless steel, rubber, etc. Body member 10 should be somewhat longer than the width of an average adult palm and, in one embodiment, is approximately four and one-half inches in length. The thickness of the thickest part of that embodiment is approximately one and one-quarter inches. It should be noted that these dimensions are by way of example only and that neither the dimensions nor the exact contours of the device as illustrated, are limiting feature of the present invention. Body member 10 is sub-divided lengthwise into two sections, a handle section 11 and a control section 12. Handle section 11 may be longitudinally ribbed, as shown, to facilitate grasping of that section without rotation in the palm of a user. Control section 12 is described in greater detail below.

A bore passage 13 extends longitudinally through body member 10 and terminates in respective nipples or projections 14, 15 at opposite ends of the body member. These nipples or projections are adapted to receive ends of IV tubing 40, 41, so that the valve may be inserted directly into an IV line. Of course, other conventional means of engaging IV tubing may be employed, the important feature being that bore passage 13 is disposed in series in the IV line.

The control section 12 of body member 10 includes a slot 16 extending longitudinally through most of the control section length from the end of the body member in which the control section is located. Slot 16 extends entirely through the thickness of the control section 12 so that the slot is open at both sides and at one end. A transverse threaded cylindrical bore 17 extends radially from bore passage 13 into communication with slot 16. Across slot 16 from the termination of bore 17, there is defined a cylindrical recess 18 which is coaxially aligned with bore 17 but smaller in diameter.

A control member 20 includes adjustment knob 21 in the form of a flat circular disc. From one side of the center of knob 21 there extends a retainer pin 22 adapted to be received in recess 18. An adjustment pin 23, threaded to engage bore 17, extends perpendicularly from the center of the opposite side of knob 21. Pins 22 and 23 are coaxially aligned but, as is the case with bore 17 and recess 18, adjustment pin 23 has a larger diameter than retainer pin 22. A gate member 24 is journaled in the end of adjustment pin 23 remote from knob 21. Gate member 24 is adapted to move transversely across bore passage 13, in adjustable degrees of flow blocking relationship, as the adjustment pin rotates in bore 17 due to rotation of adjustment knob 21. A slot 19 is defined in part of the periphery of bore passage 13 opposite bore 17 and contoured to receive the peripheral portion of gate member 24. The control member is readily inserted into position, with pin 22 in recess 18 and pin 23 in bore 17, by flexibly spreading the opposite walls of slot 16. The diameter of knob 21 is sufficiently great to permit the knob to project somewhat out of the slot 16 to permit access by a user.

The primary feature of the present invention involves a locking member 26 which is arranged to maintain adjustment knob 21 in the position to which it has been set. In the preferred embodiment illustrated, locking mechanism 26 is formed integrally with body member 10 and is located at the end of the body member which contains the control section 12. The locking member is in the form of a flap 28, secured to the body member at one side of slot 16 and arranged to pivot about a region or line at which it is secured. The other or remote end of the flap includes a projection 27, adapted to mate with and be retained in a suitably provided notch 29 located in the body member on the opposite side of slot 16 from the pivot region. A brake surface 30 is positioned to project into slot 16 and bear firmly against the rim of knob 21 when locking member 26 is closed (i.e., when projection 27 is engaged in notch 29). To further secure the locking function, the brake surface 30 and the rim of knob 21 may be ribbed or knurled, as illustrated in FIG. 4, to provide a gear-like mating arrangement.

In use, with locking arrangement 26 open, a nurse or other health care personnel grasps handle section 11 across the palm, leaving the control section 12 and, in particular knob 21, accessable between the thumb and forefinger. Knob 21 is adjusted until the desired IV flow is achieved through IV tubes 40, 41 by viewing the drip rate in a conventional manner. When the desired flow rate is achieved, locking mechanism 26 is closed by snapping projection 27 into notch 29. This forces brake surface 30 against knob 21 and precludes inadvertent movement of the knob. Moreover, the locking arrangement serves as a psychological barrier to conscious or sub-conscious twiddling of the valve by a curious patient. Since there is no clamping of a plastic tube, there is no "creep" phenomeon and the IV flow rate remains constant.

The locking mechanism need not be a brake type lock of the type described above. For example, as illustrated in FIG. 5, a detent lock arrangement may be employed whereby the rim of knob 21 is provided with a plurality of special recesses 33 and the brake surface 30 is replaced by a projection 34 adapted to be received by whichever recess 33 radially faces the projection.

It should also be noted that the in-line valve itself need not be a sluice gate type valve but may be a globe valve, butterfly valve, ball valve, etc., the important point being that the valve adjustment device can be selectively locked in place.

The particular valve described herein is advantageous in that it is very inexpensive to manufacture. The valve includes three parts, namely the body member 10, control member 20, and gate member 24. If locking member 26 is made as a separate piece (whereby it may be pivoted by a pin or the like), additional but simple parts are required. However, it is quite simple to make a pivotal locking member integral with the body member by using, for example, thin-walled polypropylene at the joint between the locking and body members. In either case, the valve is sufficiently inexpensive to justify single use disposability without sacrificing setting accuracy.

The valve assembly is inserted into an IV line between two tubes 40, 41 such as standard polyvinylchloride, flexible tigon, or like medical grade tubing at a convenient level to permit the IV drip chamber to be easily viewed. The unit may be placed in line by the supplier of the tubing 40, 41 or by a technician under sterile conditions. Tubing clamps may be provided if the connection is to be made in situ.

The present invention is not to be limited to the embodiments as herein described for numerous modifications can be made within the scope of the appended claims by a person skilled in the art without detracting the spirit of the invention.

The embodiments of the present invention in which an exclusive property or privilege is claimed are as follows:

1. A valve for controlling fluid flow through intravenous supply tubing, comprising:
   a body member having a horizontal passage extending therethrough and means for connecting said passage in series with said intravenous tubing said body member including a first mating element;
   selectively movable valving means, including a valve member disposed in said passage, for adjustably blocking flow through said passage by moving said member within said passage, said valving means including a movable actuator for said valve member at least partially received within said body member, and means securing said actuator to said body member; and
   locking means formed as an integral part of said body member, separate from said actuator and selectively pivotable independently of said actuator between open and closed positions, said locking means including a bearing surface which in said closed position bears against said actuator to prevent inadvertent movement of said valve member, said locking means in said open position being out of contact with said actuator to permit movement of said valve member said locking means further including a second mating element which engages said first mating element in said closed position.

2. The valve according to claim 1 wherein said actuator comprises a flat adjustment disc and wherein said locking means includes a brake surface which bears firmly against said disc in said closed position and is spaced from said disc in said open position.

3. The valve according to claim 2 wherein said disc includes a knurled rim and wherein said brake surface is knurled to provide a gear-like engagement with said knurled rim in said closed position of said locking means.

4. The valve according to claim 2 wherein said valving means further comprises a threaded adjustment pin extending perpendicularly from the center of said disc, and wherein said body member includes a bore which is threaded to mate with said adjustment pin and extends transversely from said passage, wherein said valve member extends from said adjustment pin, and wherein said valving means is positioned with said adjustment pin in threaded engagement with said bore and with said valve member disposed in said passage such that upon rotation of said disc said valve member moves within said passage.

5. The valve according to claims 2, 3, or 4 wherein the engagement between the first mating element of said locking means and the second mating element of said body member is a snap-fit engagement.

6. The valve according to claim 4 wherein said valve member is a sluice gate member journaled to said adjustment pin for movement transversely across said passage in response to rotational movement of said adjustment pin in said bore.

7. The valve according to claim 1 wherein said actuator comprises a series of like recesses and wherein said locking means comprises a projection for engaging said recesses individually.

8. The valve according to claim 1 wherein said body member and said locking means comprise an integral member, and wherein said valving means comprises said valve member and said actuator as its only two parts, whereby said valve is made of only three parts in total.

* * * * *